United States Patent
Shivashankara et al.

[11] Patent Number: 6,119,521
[45] Date of Patent: Sep. 19, 2000

[54] APPARATUS AND METHOD FOR MEASURING THE ACOUSTIC PROPERTIES OF ACOUSTIC ABSORBERS

[75] Inventors: Belur Shivashankara, Bellevue; Fredrick M. Hutto, Everett, both of Wash.; Noe Arcas, Plainview; Charles A. Parente, Oyster Bay, both of N.Y.; Ronald F. Olsen, Woodinville, Wash.

[73] Assignee: Northrop Grumman Corporation, Los Angeles, Calif.

[21] Appl. No.: 09/062,906

[22] Filed: Apr. 20, 1998

[51] Int. Cl.⁷ .................................................. G01N 29/04
[52] U.S. Cl. ................................................ 73/589; 181/284
[58] Field of Search ........................... 73/572, 574, 583, 73/584, 588, 589, 591, 599, 643; 181/284, 286, 290, 292, 293, 294

[56] References Cited

U.S. PATENT DOCUMENTS

| | | | |
|---|---|---|---|
| 2,015,612 | 9/1935 | Adler, Jr. | 177/337 |
| 2,419,099 | 4/1947 | Wall | 234/29.5 |
| 2,713,679 | 7/1955 | Ewertz | 340/263 |
| 2,837,914 | 6/1958 | Caldwell | 73/67.1 |
| 3,199,074 | 8/1965 | Hales et al. | 340/38 |
| 3,258,744 | 6/1966 | Auer, Jr. | 340/37 |
| 3,445,637 | 5/1969 | Auer, Jr. | 235/150.2 |
| 3,506,809 | 4/1970 | Pallat | 235/150.24 |
| 3,573,724 | 4/1971 | Komorida | 340/38 |
| 3,824,842 | 7/1974 | Wirt et al. | 73/69 |
| 3,915,016 | 10/1975 | Jhaveri et al. | 73/555 |
| 3,960,004 | 6/1976 | Wirt et al. | 73/67.1 |
| 4,235,303 | 11/1980 | Dhoore et al. | 181/214 |
| 4,305,295 | 12/1981 | Andersson et al. | 73/589 |
| 4,370,718 | 1/1983 | Chasek | 364/436 |
| 4,379,191 | 4/1983 | Beggs et al. | 428/118 |
| 4,397,187 | 8/1983 | Stribling | 73/589 |
| 4,463,453 | 7/1984 | Cohen et al. | 367/135 |
| 4,537,630 | 8/1985 | Syed | 73/589 |
| 4,651,566 | 3/1987 | Andersson et al. | 73/589 |
| 4,674,069 | 6/1987 | Mizuno | 367/90 |
| 4,732,039 | 3/1988 | Syed | 73/589 |
| 4,768,379 | 9/1988 | Arcas et al. | 73/589 |
| 5,377,546 | 1/1995 | Arcas et al. | 73/589 |
| 5,684,251 | 11/1997 | Arcas et al. | 73/589 |

*Primary Examiner*—Hezron Williams
*Assistant Examiner*—Rose M. Miller
*Attorney, Agent, or Firm*—Terry J. Anderson; Karl J. Hoch, Jr.

[57] ABSTRACT

A device for measuring the acoustic absorption properties of materials such as liners for jet engines has a first housing, an acoustic driver configured to provide acoustic energy to the first housing, a second housing attached to the first housing, and an acoustic driver configured to provide acoustic energy to the second housing. Acoustic sensors are used to measure the acoustic energy emitted from the two housings and to measure the absorption of each of the housings.

42 Claims, 3 Drawing Sheets

APPARATUS AND METHOD FOR MEASURING THE ACOUSTIC PROPERTIES OF ACOUSTIC ABSORBERS

FIELD OF THE INVENTION

The present invention relates generally to noise measurement and more particularly to an apparatus and method for measuring the acoustic absorption properties of acoustic absorbers, particularly for absorber configurations utilized in the construction of jet engine inlet and/or exhaust acoustic liners with acoustically coupled cavities.

BACKGROUND OF THE INVENTION

In order to mitigate the noise generated by a jet engine, it is known to form the jet engine inlet and exhaust duct walls of noise absorbing material. This is particularly desirable for commercial passenger aircraft, since such aircraft are required to meet stringent government noise regulations. Such noise suppression for commercial passenger aircraft is also desirable so as to enhance the comfort of the passengers thereof.

Additionally, many localities have noise regulations which limit the amount of noise that an aircraft may make in order to prevent annoying nearby residents. This sometimes limits the types of aircraft that may utilize a particular airport. It also frequently imposes procedural restrictions upon aircraft which would otherwise be undesirable. For example, aircraft may be required to fly over designated neighborhoods at a prescribed minimum altitude. Flying at such a minimum altitude may undesirably increase fuel consumption and also possibly accelerate engine wear (particularly when the minimum altitude must be reached immediately after takeoff).

According to contemporary methodology, a noise suppressing material sold under the name DYNAROHR (a registered trademark of Rohr Industries, Inc.) is utilized extensively of this purpose. The DYNAROHR product is formed of a honeycomb material which is disclosed in U.S. Pat. No. 4,379,191, the contents of which are hereby incorporated by reference. This honeycomb material comprises a core having a plurality of open cells. The core is sandwiched between an outer non-porous layer and an inner porous layer. The inner porous layer is in fluid communication with the open cells of the honeycomb material. A microporous sheet material, such as one comprised of finely woven stainless steel cloth, is bonded over the porous sheet and forms a part of the inner surface of the jet engine's inlet duct.

As those skilled in the art will appreciate, at least a portion of the acoustic energy incident on such noise suppression material is not absorbed but is re-radiated elsewhere. The intensity of the re-radiated acoustic energy provides a measure of the absorption or effectiveness of the noise suppressing material.

Various devices and methodologies are well known for measuring the acoustic absorption properties of materials. For example, one such methodology comprises disposing the sound absorbent material in an anechoic chamber proximate a sound source and a sound sensor, and then making sound measurements both with the material in place and removed, such that a comparison of the sound measurements may be made. However, as those skilled in the art will appreciate, such contemporary methodology requires the use of an anechoic chamber, which is inconvenient, expensive, not easily transported, and incapable of utilizing the high sound levels generated in the intake of a commercial jet engine.

As such, it is beneficial to provide means for testing the acoustic absorption properties of materials, wherein such means are convenient to use, inexpensive, and transportable, such that material samples may be tested without requiring the use of an anechoic chamber.

SUMMARY OF THE INVENTION

The present invention specifically addresses and alleviates the above mentioned deficiencies associated with the prior art. More particularly, the present invention comprises a device for measuring the acoustic absorption properties of materials with acoustically coupled cavities. The device comprises a first housing, preferably configured as a tube, an acoustic driver configured to provide acoustic energy to the first housing, acoustic sensors configured to sense acoustic energy within the first housing, a second housing, also preferably configured as a tube, and acoustic sensors configured to sense acoustic energy within the second housing. Acoustic energy emitted from the first and second housing travels through the material being tested and is reflected back to the first and second housing where it is sensed. The present invention is particularly suitable for measuring effectiveness of acoustic liners which absorb acoustic energy, and re-radiate a portion of the acoustic energy.

More particularly, the present invention generally comprises a first tube having proximal and distal ends, a first acoustic driver configured to provide acoustic energy to the first tube, at least two acoustic sensors configured to sense acoustic energy within the first tube, a second tube having a proximal and distal ends, a second acoustic driver configured to provide acoustic energy to the second tube, and at least two acoustic sensors configured to sense acoustic energy within the second tube. The first and second tubes cooperate to provide two sources of acoustic energy having a desired phase difference therebetween so as to substantially simulate an acoustic condition to which the material is to actually be exposed.

As those skilled in the art will appreciate, sound suppressing material or acoustic liners are typically exposed to acoustic energy wherein different portions of a wave front are incident upon different portions of the liner at a given time, thus causing different portions of the liner to absorb portions of the acoustic energy which are out of phase with respect to one another. The present invention simulates the presence of wave fronts having phase differences by providing two acoustic drivers which may be driven at desired phase relationship with respect to one another, such that an acoustic signal having the desired phase differences is provided to the material being tested.

According to the preferred embodiment of the present invention, the first and second tubes are disposed proximate one another, preferably such that they share a common wall. Thus, the first and second tubes are preferably generally parallel to one another.

According to one preferred configuration of the present invention, the first and second tubes are configured to generally define a Y. Distal end portions of the first and second tubes define a bifurcated upper portion of the Y, and proximal end portions of a first and second tubes define a lower portion of the Y. The first and second tubes are open at the proximal end thereof and are closed at the distal end thereof, such that acoustic radiation provided within the first and second tubes tends to be radiated toward the proximal end of the device, where the material being tested is disposed.

The first and second acoustic drivers preferably comprise speakers and are preferably disposed proximate the distal ends of the first and second tubes, respectively. According to the preferred embodiment of the present invention, the first and second drivers are disposed at the distal ends of the first and second tubes and are oriented such that they radiate acoustic energy along a generally longitudinal axis thereof, i.e., generally toward the material being tested.

The first and second acoustic sensors are preferably disposed proximate the proximal end of the first and second tubes, respectively. The first and second acoustic sensors preferably comprise microphones. Alternatively, the first and second acoustic sensors comprise pressure transducers.

Preferably, the present invention comprises two first acoustic sensors, both disposed within the first tube and two second acoustic sensors, both disposed within the second tube. The first two acoustic sensors are preferably spaced apart along the longitudinal axis of the tube and the second two acoustic sensors are similarly spaced apart along the longitudinal axis of the second tube such that each pair of acoustic sensors senses the acoustic incident energy and radiated energy, thereby facilitating the separation of the acoustic signal radiated by the drivers from the acoustic signal radiated by the material being tested via a two channel spectrum analyzer according to principles well known in the art.

A mixing chamber is disposed or formed at the proximal end of a first and second tubes for mounting porous material while also facilitating mixing acoustic energy from the first and second tubes together. Thus, acoustic energy from the first tube is mixed, to a desired degree, with acoustic energy from the second tube, while being incident upon the material being tested. Such mixing provides a more realistic simulation of the acoustic conditions actually encountered during use of jet engine acoustic liners with acoustically coupled chambers and the like.

The mixing chamber preferably comprises a porous partition through which acoustic energy passes between the two cavities of the mixing chamber. The porous partition is preferably disposed intermediate the mixing chamber and the first and second tubes. According to the preferred embodiment of the present invention, the porous partition is removably attached to the mixing chamber and the mixing chamber is configured such that the porous partition is easily removed and replaced, thereby facilitating changing thereof among a plurality of different porous partitions, each having a different porosity.

A system for measuring acoustic absorption properties of material further comprises a circuit for driving first and second acoustic drivers such that the first and second acoustic drivers are substantially out of phase with one another and a circuit for analyzing the outputs from the first and second acoustic sensors. The circuit for driving the first and second acoustic drivers such that a phase difference of the first and second acoustic drivers is obtained is preferably controllable such that the phase difference between the first and second acoustic drivers can be set, as desired.

A dual channel spectrum analyzer is preferably utilized for analyzing the outputs from the first and second acoustic sensors, thereby facilitating the separation of the driver signal, i.e., that signal provided by the drivers prior to its being incident upon the material being tested, from the signal radiated from the material being tested, thereby facilitating more accurate measurement of the signal being radiated from the material being tested. By more accurately measuring the signal being radiated from the material being tested, a more accurate determination of the acoustic properties of the material being tested is provided.

These, as well as other advantages of the present invention, will be more apparent from the following description and drawings. It is understood that changes in the specific structure shown and described may be made within the scope of the claims without departing from the spirit of the invention.

BRIEF DESCRIPTION OF THE DRAWINGS

FIG. 3b is a side view of the mixing chamber of FIG. 3a;

DETAILED DESCRIPTION OF THE PREFERRED INVENTION

The detailed description set forth below in connection with the appended drawings is intended as description of the presently preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
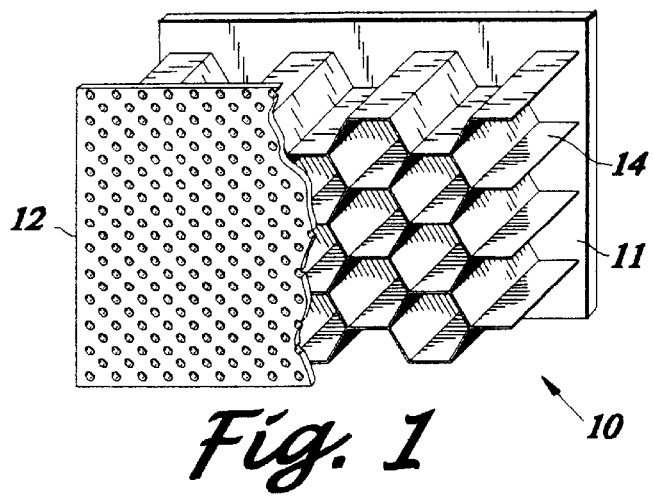
FIG. 1 is a perspective view of a typical jet engine acoustic liner.
Figure 3A:
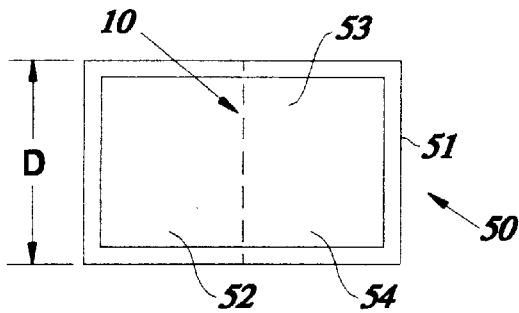
FIG. 3a is a top view of a mixing chamber for use with the present invention, showing the material being tested in dashed lines.
Figure 3B:
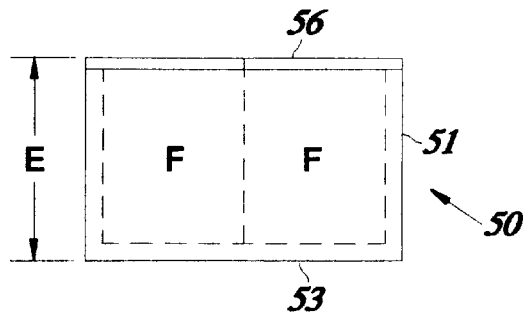
Figure 4:
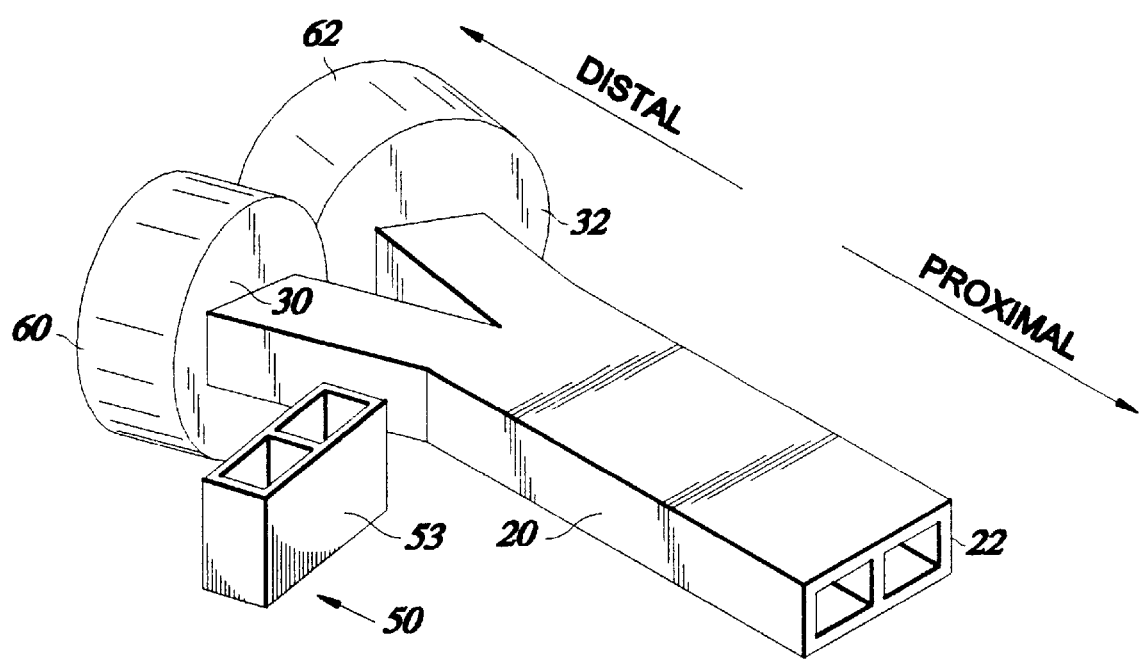
FIG. 4 is a perspective view of a second embodiment of the present invention wherein the first and second tubes cooperate to define a Y.

The device for measuring acoustic absorption properties of material of the present invention is illustrated in FIGS. 2–5 which depict two presently preferred embodiments thereof. FIG. 1 depicts a typical jet engine acoustic liner. FIGS. 2a–3b depict a first embodiment of the present invention and FIG. 4 depicts a second embodiment thereof.

Referring now to FIG. 1, a typical jet engine acoustic liner generally comprises a non-porous outer layer 11, a porous inner layer 12, and a honeycomb core 14. As those skilled in the art will appreciate, the porous inner layer 12 may either comprise linear (micro-porous) or non-linear (perforate) openings. The non-porous outer layer 11, the porous inner layer 12, and the honeycomb core 14 may be made of a variety of different materials such as aluminum, polymer, and/or composite materials.

Various different configurations of these materials are possible. For example, various thicknesses of the outer layer 11 and inner layer 12, as well as the honeycomb core 14 are possible. Further, various different porosities of the inner layers 12 and various different cell sizes and configurations of the honeycomb core 14 are possible. Thus, it is frequently desirable to measure the effectiveness of the sound absorption of such sound suppressing materials due to the wide range of configurations possible.

Figure 2A:
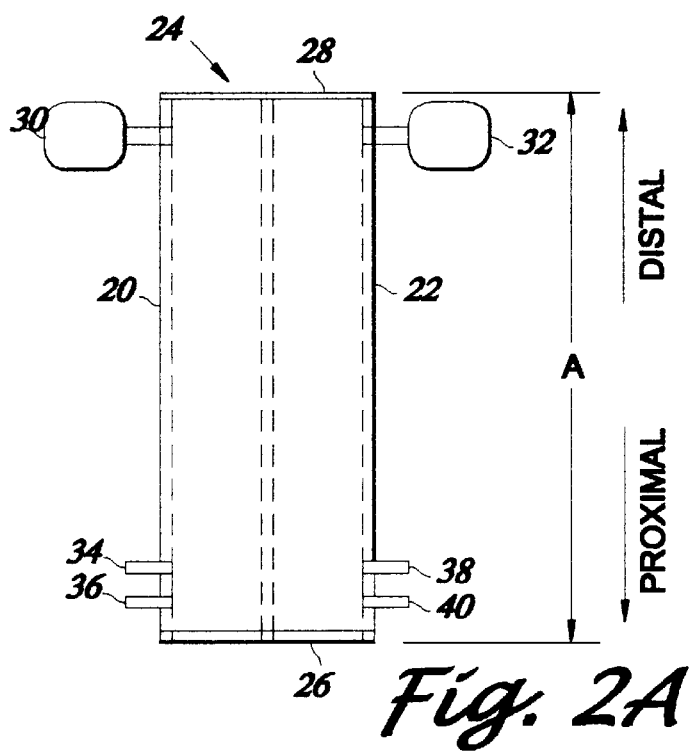
FIG. 2a is a side view of a first preferred embodiment of the present invention wherein the tubes are generally linear in configuration and the acoustic drivers are attached at right angles to the distal ends of the tubes.
Figure 2B:
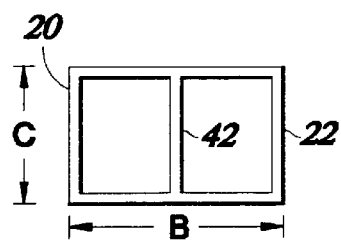
FIG. 2b is an end view of the device of FIG. 2a, as seen from the proximal end thereof.

Referring now to FIGS. 2a, and 2b, the first embodiment of the device for measuring the absorption of properties of material of the first embodiment generally comprises a first housing or tube 20 attached to and/or formed with a second housing or tube 22. Both the first 20 and second 22 tubes are closed at the distal end 24 thereof and are open at the proximal end 26 thereof. Thus, cover 28 seals the distal end of the first 20 and second 22 tubes. Cover 28 is preferably easily removable, so as to facilitate access to the distal portion of the inside of the first 20 and second 22 tubes.

First acoustic driver, preferably a speaker 30 is configured so as to provide acoustic energy to the distal end of the first tube 20. Similarly, second acoustic driver or speaker 32 is configured to provide acoustic energy to the distal end of the second tube 22.

Two first pressure transducers or microphones 34, 36 are configured to sense the intensity of acoustic energy within the first tube 20, proximate the proximal end 26 thereof. Similarly, two second microphones 38, 40 are positioned proximate the proximal end 26 of the second tube 22 and are configured to sense the intensity of acoustic energy therein.

According to the preferred embodiment of the present invention the first 20 and second 22 tubes are generally rectangular in cross section, as best shown in FIG. 2b. The first 20 and second 22 tubes preferably comprise a common wall 42. However, as those skilled in the art will appreciate, various different configurations of a first 20 and second 22 tubes are suitable. For example, the first 20 and second 22 tubes may comprise totally independent structures, i.e., not sharing any common portions thereof. The orientation of the first 20 and second 22 tubes may vary substantially from that shown in FIGS. 2a, and 2b. For example, the first 20 and second 22 tubes shown in FIGS. 2a and 2b are formed along parallel longitudinal axes. However, the first 20 and second 22 tubes may be formed along non-parallel axes. Indeed, if the first 20 and second 22 tubes are formed independently of one another, i.e., are not attached to one another, the longitudinal axis thereof may be varied, as desired.

The length, dimension A, of the first 20 and second 22 tubes is preferably approximately 10 inches. The width, dimension B, is preferably three inches and the depth, dimension C, is preferably approximately 1.5 inches. The wall thickness of the first and second 22 tube need only be sufficient so as to insure structural integrity and prevent excessive leakage of acoustic energy therethrough. Those skilled in the art will appreciate that various different dimensions may be utilized, particularly so as to accommodate the testing of materials having various different dimensions. Various different materials, i.e., aluminum, polymer, composite, etc., may be utilized to construct the first 20, and second 22 tubes and the wall thickness will depend upon the particular material utilized. Typical wall thickness will generally be between approximately 5.0 mm and 10 mm.

Referring now to FIG. 3a, the device for measuring acoustic absorption of the present invention preferably comprises a mixing chamber 50 for mixing acoustic radiation from the first 20 and second 22 tubes together so as to more realistically simulate the actual conditions of the acoustic environment in which the absorber being tested is to be utilized. The mixing chamber 50 comprises sides or walls 51 and the bottom or floor 53. The mixing chamber 50 conforms generally in shape and configuration to the first 20 and second 22 tubes such that acoustic energy from the first tube 20 enters a first portion 52 of the mixing chamber 50 and acoustic energy from the second tube 22 enters a second portion 54 of the mixing chamber 50.

The first 52 and second 54 portions of the mixing chamber 50 are divided by a porous piece of test material 10, the acoustic properties of which are to be tested. Thus, a coupon or section of the acoustic absorption material which the effect of acoustically coupling the chambers are desired to be measured is placed within the mixing chamber 50 such that it substantially divides the mixing chamber 50 into first 52 and second 54 portions. Thus, as those skilled in the art will appreciate, acoustic energy from the first 52 portion of the acoustic mixing chamber 50 passes through the material 10 and, similarly, a portion of the acoustic energy within the second portion 54 of the acoustic mixing chamber 50 passes through the material 10 into the first portion 52. As acoustic energy passes through the test material 10, some portion of the acoustic energy is absorbed by the material 10. The present invention facilitates measurement of that additional portion of the acoustic energy absorbed by the material 10 for the absorber configuration.

The mixing chamber 50 is preferably configured for easy removal and replacement of the material 10. Preferably, the walls 51 of the mixing chamber 50 comprise slots into which the test material 10 slides, so as to remain in position within the mixing chamber 50 during testing. Those skilled in the art will appreciate that various other means for mounting the material 10 within the mixing chamber 50 are likewise suitable.

A linear face sheet 56 preferably covers the openings formed in the mixing chamber 50 and forms an interface between the mixing chamber 50 and the first 20 and second 22 tubes. The linear face sheet 56 coupled with the common wall material 10 provides a degree of attenuation to the acoustic signals within the first 20 and second 22 tubes.

The mixing chamber 50 is preferably formed of similar materials to the first 20 and second 22 tubes and preferably conforms in cross section thereto, so as to facilitate easy interfacing of the first 20 and second 22 tubes to the mixing chamber 50. Thus, according to the preferred embodiment of the present invention, the width of the mixing chamber 50 is approximately 3 inches, with the first 52 and second 54 portions thereof each having a width, dimension F, of approximately 1.5 inches, and the depth, dimension D, of the mixing chamber 50 is approximately 1.5 inches. The mixing chamber 50 is approximately 1.5 inches in height, dimension E.

Referring now to FIG. 4, according to a second embodiment of the present invention the distal ends 60 and 62 of the first 20 and second 22 tubes split away from one another so as to generally define a Y. The first 30 and second 32 acoustic drivers or speakers are disposed at the distal ends and a first 20 and second 22 tubes so as to direct acoustic energy generally along the longitudinal axes of the first 20 and second 22 tubes. Thus, the second embodiment of the present invention is more efficient at delivering acoustic energy from the acoustic drivers 30, 32 to the tubes 20, 22.

Figure 5:
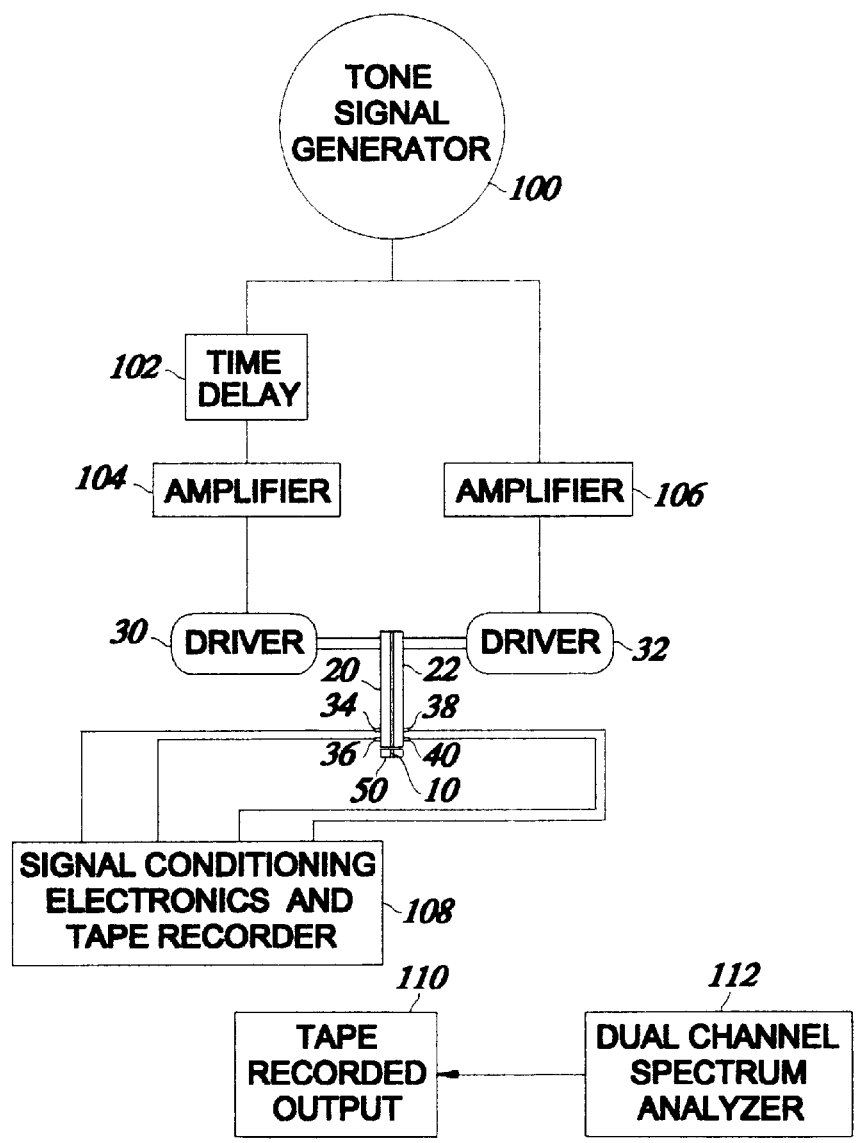
FIG. 5 is an electrical block diagram of the circuitry associated with the first and second embodiments of the present invention.

Referring now to FIG. 5, according to the preferred embodiments of the present invention a pure tone signal generator 100 provides an electrical drive signal to the first 30 and second 32 drivers or speakers. The electrical signal is provided from a pure tone signal generator 100 through time delay 102 and amplifier 104 to the first speaker 30 and through amplifier 106 to the second speaker 32. Thus, the time delay 102 may be utilized to effect a phase difference between the drive signals provided to the first 30 and second 32 speakers, such that acoustic energy within the first 20 and second 22 tubes is controllable.

Signal conditioning electronics and tape recorder 108 facilitate the sensing and recording of the acoustic signals within the first 20 and second 22 tubes. The tape recorder output 110 may be provided, at a later time, i.e., subsequent to testing, to dual channel spectrum analyzer 112 for analysis thereof. Such analysis facilitates the separation of the composite acoustic signals into the components thereof, as discussed in detail below.

Having discussed the structure of the device for measuring the acoustic absorption properties of acoustic absorbers of the present invention, it may be beneficial to describe the operation thereof. According to the present invention, the material 10 is inserted into the test chamber 50 so as to form a partition between the first 52 and second 54 portions of the test chamber 50. The test chamber 50 is then interfaced, i.e., attached or placed in contact with the proximal end of the first 20 and second 22 tubes such that the first tube 20 is in acoustic communication with the first portion 52 of the mixing chamber 50 and the second tube 22 is in acoustic communication with the second portion 54 of the mixing chamber 50, both preferably via the linear face sheet 56 of the mixing chamber 50.

The pure tone signal generator 100 is then used to drive speakers 30 and 32. The time delay 102 is adjusted so as to provide the desired phase difference between the acoustic tone by the first 30 and second 32 speakers. Amplifiers 104 and 106 are adjusted so as to provide the desired amplitudes of the acoustic tone generated by the first 30 and second 32 speakers.

After the amplitude of the acoustic signal generated by the first 30 and second 32 speakers and the phase difference therebetween has been adjusted, as desired, then the signal sensed by the two first microphones 34, 36 and the two second microphones 38, 40 are all recorded via the signal conditioning electronics and tape recorder 108.

At a subsequent time the tape recorded outputs 110 are provided to dual channel spectrum analyzer 112 so as to facilitate analysis thereof. Analysis preferably comprises separating the composite acoustic signals into components representative to the acoustic energy incident and reflected by the acoustic absorber, i.e. the material 10.

As those skilled in the art will appreciate, it is possible to separate the composite acoustic signals into their components utilizing two spaced apart microphones such as 34 and 36 or 38 and 40 since the electrical signals generated thereby provide four equations in four unknowns. Thus, the spacing of the two microphones 34, 36 in the first tube 20 facilitates the determination of that part of the acoustic energy which is absorbed by the first portion 52 of the chamber 50, and likewise the spaced apart microphones 38 and 34 of the second tube 22 facilitate the determination of that part of the acoustic energy which is absorbed by the second portion 54 of the chamber 50.

It is understood that the exemplary device for measuring the acoustic absorption properties of materials described herein and shown in the drawings represents only the presently preferred embodiments of the invention. Indeed, various modifications and additions may be made to such embodiments without departing from the spirit and scope of the invention. For example, the tubes may be of various different cross-sectional configurations, e.g., round, oval, triangular, square, rectangular, pentagonal, hexagonal, octagonal, etc. Further, various different shapes of the mixing chamber are contemplated.

Thus, these and other modifications and additions may be obvious to those skilled in the art and may be implemented to adapt the present invention for use in a variety of different applications.

What is claimed is:

1. A device for measuring acoustic absorption properties of an acoustic absorber, the device comprising:
    a) a first tube having proximal and distal ends;
    b) a first acoustic driver configured to provide acoustic energy to the first tube;
    c) at least one first acoustic sensor configured to sense acoustic energy within the first tube and operative to generate an output corresponding thereto;
    d) a second tube having proximal and distal ends;
    e) a second acoustic driver configured to provide acoustic energy to the second tube;
    f) at least one second acoustic sensor configured to provide acoustic energy to the second tube and operative to generate an output corresponding thereto;
    g) wherein the first and second tubes cooperate to provide two sources of acoustic energy having a desired phase difference therebetween to substantially simulate an acoustic condition to which the acoustic absorber may be exposed for purposes of measuring the acoustic absorption properties thereof.

2. The device as recited in claim 1, wherein the first and second tubes are disposed proximate one another.

3. The device as recited in claim 1, wherein the first and second tubes comprise a common wall.

4. The device as recited in claim 1, wherein the first and second tubes are generally parallel to one another.

5. The device as recited in claim 1, wherein the first and second tubes are configured to generally define a Y, distal end portions of the first and second tubes defining a bifurcated upper portion of the Y and proximal end portions of the first and second tubes defining a lower portion of the Y.

6. The device as recited in claim 1, wherein the first and second tubes are open at the proximal end and are closed at the distal end thereof.

7. The device as recited in claim 1, wherein the first and second acoustic drivers comprise speakers.

8. The device as recited in claim 1, wherein the first and second acoustic drivers are disposed proximate the distal ends of the first and second tubes, respectively.

9. The device as recited in claim 1, wherein the first and second acoustic sensors are disposed proximate the proximal ends of the first and second tubes, respectively.

10. The device as recited in claim 1, wherein the first and second acoustic sensors comprise microphones.

11. The device as recited in claim 1, wherein the first and second acoustic sensors comprise pressure transducers.

12. The device as recited in claim 1, wherein the at least one first acoustic sensor comprises two first acoustic sensors and the at least one second acoustic sensor comprises two second acoustic sensors.

13. The device as recited in claim 12, wherein the two first acoustic sensors are spaced apart along a longitudinal axis of the first tube and the two second acoustic sensors are space apart along a longitudinal axis of the second tube.

14. The device as recited in claim 1, further comprising a mixing chamber disposed at the proximal end of the first and second tubes for mounting the acoustic absorber such that acoustic energy from the first tube passes through the acoustic absorber and enters the second tube and acoustic energy from the second tube passes through the acoustic absorber and enters the first tube.

15. The device as recited in claim 1, further comprising a mixing chamber disposed at the proximal end of the first and second tubes for mixing acoustic energy from the first and second tubes, the acoustic absorber being mountable within the mixing chamber such that acoustic energy passes therethrough to effect mixing thereof.

16. The device as recited in claim 1, further comprising a mixing chamber disposed at the proximal end of the first and second tubes for mixing acoustic energy from the first and second tubes, the acoustic absorber being mountable within the mixing chamber such that acoustic energy passes therethrough to effect mixing thereof, the mixing chamber being configured for easy removal and replacement of the acoustic absorber so as to facilitate changing thereof.

17. The device as recited in claim 1, further comprising:
   a) a circuit for driving the first and second acoustic drivers such that the first and second acoustic drivers are substantially out of phase with one another; and
   b) a circuit for analyzing the outputs from the first and second acoustic sensors.

18. The device as recited in claim 1, further comprising:
   a) a circuit for driving the first and second acoustic drivers such that a phase difference of the first and second acoustic drivers is controllable; and
   b) a dual channel spectrum analyzer for analyzing the outputs from the first and second acoustic sensors.

19. A system for measuring acoustic absorption properties of an acoustic absorber, the system comprising:
   a) a first tube having proximal and distal ends;
   b) a first acoustic driver configured to provide acoustic energy to the first tube;
   c) at least one acoustic sensor configured to sense acoustic energy within the first tube;
   d) a second tube having proximal and distal ends;
   e) a second acoustic driver configured to provide acoustic energy to the second tube;
   f) at least one acoustic sensor configured to sense acoustic energy within the second tube; and
   g) a mixing chamber disposed at the proximal ends of the first and second tubes for mixing acoustic energy from the first and second tubes and for applying acoustic energy to the acoustic absorber for purposes of measuring the acoustic absorption properties thereof, the acoustic absorber being mountable within the mixing chamber such that acoustic energy passes therethrough to effect mixing thereof.

20. A method for measuring acoustic absorption properties of an acoustic absorber, the method comprising:
   a) providing first and second housings, the first and second housings being proximate to one another;
   b) mounting the acoustic absorber in a location between the first and second housings;
   c) providing acoustic energy from an acoustic driver to the first housing such that acoustic energy travels from the first housing through the acoustic absorber, and enters the second housing; and,
   d) sensing acoustic energy that enters the second housing.

21. A method for measuring acoustic absorption properties of an acoustic absorber, the method comprising the steps of:
   a) providing first and second tubes having proximal and distal ends, each of the first and second tubes having an acoustic driver in acoustic communication therewith and also having at least one acoustic sensor in acoustic communication therewith;
   b) mounting the acoustic absorber in a location between the first and second tubes;
   c) generating acoustic energy with the acoustic drivers of the first and second tubes such that acoustic energy travels through the first and second tubes and into the acoustic absorber therebetween; and
   d) sensing acoustic energy traveling from the acoustic absorber into the first and second tubes via the acoustic sensors to measure the acoustic absorption properties of the acoustic absorber.

22. The method as recited in claim 21, wherein the first and second tubes cooperate to provide two sources of acoustic energy having a desired phase difference to substantially simulate an acoustic condition to which the acoustic absorber is to be exposed.

23. The method as recited in claim 21, wherein the first and second tubes are disposed proximate one another.

24. The method of claim 21, wherein the first and second tubes comprise a common wall.

25. The method of claim 21, wherein the first and second tubes are generally parallel to one another.

26. The method of claim 21, wherein the first and second tubes are configured to generally define a Y, distal end portions of the first and second tubes defining a bifurcated upper portion of the Y and proximal end portions of the first and second tubes defining a lower portion of the Y.

27. The method of claim 21, wherein the first and second tubes are open at the proximal ends thereof and are closed at the distal ends thereof.

28. The method of claim 21, wherein the acoustic drivers of the first and second tubes comprise speakers.

29. The method of claim 21, wherein the acoustic drivers of the first and second tubes are disposed proximate the distal ends of the first and second tubes, respectively.

30. The method of claim 21, wherein the acoustic sensors of the first and second tubes are disposed proximate the proximal ends of the first and second tubes, respectively.

31. The method of claim 21, wherein the acoustic sensors of the first and second tubes comprise microphones.

32. The method of claim 21, wherein the acoustic sensors of the first and second tubes comprise pressure transducers.

33. The method of claim 21, wherein the first and second tubes each include two acoustic sensors.

34. The method of claim 33, wherein the two acoustic sensors of the first tube are spaced apart along a longitudinal axis of the first tube and the two acoustic sensors of the second tube are spaced apart along a longitudinal axis of the second tube.

35. The method of claim 21, further comprising the step of mixing acoustic energy from the first and second tubes.

36. The method of claim 21, further comprising the step of mixing acoustic energy from first and second tubes via a mixing chamber, the acoustic absorber being mounted within the mixing chamber such that acoustic energy passes therethrough to effect mixing thereof.

37. The method of claim 21, further comprising the step of mixing acoustic energy from the first and second tubes via a mixing chamber disposed at the proximal ends of the first and second tubes, the acoustic absorber being mounted within the mixing chamber such that acoustic energy passes therethrough to effect mixing thereof, the mixing chamber being configured for easy removal and replacement of the acoustic absorber so as to facilitate changing thereof.

38. The method of claim 21, further comprising the steps of:
   a) driving the acoustic drivers of the first and second tubes such that the acoustic drivers are substantially out of phase with one another; and
   b) analyzing outputs from the acoustic sensors of the first and second tubes.

39. The method of claim 21, further comprising the steps of:

a) controlling a phase difference of the acoustic drivers of the first and second tubes; and b) analyzing outputs from the acoustic sensors of the first and second tubes.

40. The method of claim 21, wherein the step of generating acoustic energy with the acoustic drivers comprises generating at least two acoustic signals which are out of phase with one another.

41. The method of claim 21, wherein the step of sensing acoustic energy traveling from the acoustic absorber comprises sensing the acoustic energy via two acoustic sensors for each tube so as to facilitate determination of the intensity of acoustic energy transmitted through the acoustic absorber.

42. A method for measuring acoustic absorption properties of an acoustic absorber, the method comprising the steps of:

a) providing a first tube having proximal and distal ends;

b) providing acoustic energy within the first tube;

c) sensing acoustic energy with the first tube;

d) providing a second tube having proximal and distal ends;

e) providing acoustic energy within the second tube;

f) sensing acoustic energy with the second tube; and, g) measuring the acoustic absorption properties of the acoustic absorber by mixing acoustic energy from the first and second tubes by causing the acoustic energy to pass through the acoustic absorber.

* * * * *